US006586251B2

(12) United States Patent
Economides et al.

(10) Patent No.: US 6,586,251 B2
(45) Date of Patent: Jul. 1, 2003

(54) METHODS OF MODIFYING EUKARYOTIC CELLS

(75) Inventors: Aris N. Economides, Tarrytown, NY (US); Andrew J. Murphy, Croton-on-Hudson, NY (US); David M. Valenzuela, Yorktown Heights, NY (US); George D. Yancopoulos, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 09/732,234

(22) Filed: Dec. 7, 2000

(65) Prior Publication Data

US 2002/0106628 A1 Aug. 8, 2002

Related U.S. Application Data

(60) Provisional application No. 60/244,665, filed on Oct. 31, 2000.

(51) Int. Cl.$^7$ .......................... C12N 15/87; C12N 5/00; C12N 15/00; C12N 5/06; A01K 67/027

(52) U.S. Cl. ...................... 435/463; 435/325; 435/462; 435/440; 435/352; 435/354; 800/18; 800/13; 800/14

(58) Field of Search ........................... 435/172.3, 320.1, 435/328, 372.3, 69.1, 70.21, 325, 36, 463, 462, 440, 352, 354; 536/23.1, 23.51; 800/18, 13, 14

(56) References Cited

U.S. PATENT DOCUMENTS

5,436,149 A 7/1995 Barnes ........................ 435/194
5,789,215 A 8/1998 Berns et al. .................. 800/25

FOREIGN PATENT DOCUMENTS

WO  WO 9402602  *  2/1994

OTHER PUBLICATIONS

Para et al.; Human embryonic stem cells, 2000, Journal of Cell Science 113: 5–10.*
Moreadith et.al.; Gene targeting in embryonic stem cells: the new physiology and metabolism, 1997, J. Moi. Med. 75: 208–216.*
Mullins et.al.; Perspectives Series: Molecular Medicine in Genetically Engineered Animals, 1996, J. Clin. Invest., vol. 97: 1557–1560.*
Nature, vol. 317, 1985, Smithies, O., et al., "Insertion of DNA sequences into the human chromosomal ss–globin locus by homologous recombination," pp. 230–234.
Cell, vol. 51, 1987, Thomas, K.R., and Capecchi, M.R., "Site–Directed Mutagenesis by Gene Targeting in Mouse Embryo–Derived Stem Cells," pp. 503–512.

Proc. Natl. Acad. Sci. USA, vol. 86, 1989, Koller, B.H., et al., "Germ–line transmission of a planned alteration made in a hypoxanthine phosphoribosyltransferase gene by homologous recombination in embryonic stem cells," pp. 8927–8931.
Science, vol. 254, 1991, Kuhn, R., et al., "Generation and Analysis of Interleukin–4 Deficient Mice," pp. 707–710.
Nature, vol. 346, 1990, Thomas, K.R., and Capecchi, M.R., "Targeted disruption of the murine int–1 proto–oncogene resulting in severe abnormalities in midbrain and *cerebellar development*," pp. 847–850.
Science, vol. 246, 1989, Scwartzberg, P.L., et al., "Germ–line Transmission of c–abl Mutation produced by Targeted Gene Disruption in ES Cells," pp. 799–803.
Nature, vol. 330, 1987, Doetschman, T., et al., "Targetted correction of a mutant HPRT gene in mouse embryonic stem cells," pp. 576–578.
Cell, vol. 56, 1989, Thompson, S., et al., "Germ Line Transmission and Expression of a Corrected HPRT Gene Produced by Gene Targeting in Embryonic stem Cells," pp. 313–321.
Nature, vol. 345, 1990, DeChiara, T.M., et al., "A growth–deficiency phenotype in heterozygous mice carrying an insulin–like growth factor II gene disrupted by targeting," pp. 78–80.
Nature, vol. 369, 1994, Cheng, S., et al., "Long PCR," pp. 684–685.
PCR Methods and Applications, 1994, Foord, O.S., and Rose, E.A., "Long–distance PCR," pp. 3:S149–S161.
Nucleic Acids Research, vol. 20 No. 3, 1992, Ponce, M.R., and Micol, J.L., "PCR amplification of long DNA fragments," p. 623.
Gene Targeting–A Practical Approach, $2^{nd}$ Ed., 2000, Edited by Joyner, A.L., Hasty, P. et al., Chapter 1 "Gene targeting, principles, and practice in mammalian cells," pp. 1–35.

(List continued on next page.)

*Primary Examiner*—Deborah Crouch
*Assistant Examiner*—Thaian Ton
(74) *Attorney, Agent, or Firm*—Linda O. Palladino; Gail M. Kempler

(57) ABSTRACT

A method for engineering and utilizing large DNA vectors to target, via homologous recombination, and modify, in any desirable fashion, endogenous genes and chromosomal loci in eukaryotic cells. These large DNA targeting vectors for eukaryotic cells, termed LTVECs, are derived from fragments of cloned genomic DNA larger than those typically used by other approaches intended to perform homologous targeting in eukaryotic cells. Also provided is a rapid and convenient method of detecting eukaryotic cells in which the LTVEC has correctly targeted and modified the desired endogenous gene(s) or chromosomal locus (loci) as well as the use of these cells to generate organisms bearing the genetic modification.

14 Claims, 6 Drawing Sheets

OTHER PUBLICATIONS

Molecular and Cellular Biology, vol. 12 No. 8, 1992, Deng, C., and Capecchi, M.R., "Reexamination of Gene Targeting Frequency as a Function of the Extent of Homolgy between the Targeting Vector and the Target Locus," pp. 3365–3371.

Nature Genetics, vol. 20, 1998, Zhang, Y., et al., "A new logic for DNA engineering using recombination in *Escherichia coli*," pp. 123–128.

Nucleic Acids Research, vol. 27, 1999, Angrand, P., et al, "Simplified generation of targeting constructs using ET recombination," pp. 16(e).

Nucleic Acids Research, vol. 27, 1999, Muyrers, J.P., et al., "Rapid modification of bacterial artificial chromosomes by ET–recombination," pp. 1555–1557.

Gene Therapy, vol. 6, 1999, Narayanan, K. et al., "Efficient and precise engineering of a 200kb ss–globin human/bacterial artificial chromosome in *E. coli* DH10B using an inducible homologous recombination system," pp. 442–447.

Genomics, vol. 64, 1999, HIll, F., et al., "BAC Trimming: Minimizing Clone Overlaps," pp. 111–113.

Nature Biotechnology, vol. 15, 1997, Yang, X, et al., "Homologous recombination based modification in *Escherichia coli* and germline transmission in transgenic mice of a bacterial artificial chromosome," pp. 859–865.

Proc. Natl. Acad. Sci. USA, vol. 97, 2000, Yu, D., et al., "An efficient recombination system for chromosome engineering in *Escherichia coli*," pp. 5978–5983.

Proc. Natl. Acad. Sci. USA, vol. 91, 1994, Hall, S. D, and Kolodner, R.D., "Homologous pairing and strand exchange promoted by the *Escherichia coli* RecT protein," pp. 3205–3209.

Gene, vol. 138, 1994, Kusano, K., et al., "Involvement of RecE and RectT annealing protein in DNA double–stranded break repair by homologous recombination," pp. 17–25.

Science, vol. 277, 1997, Kovall, R, and Matthews, B.W., "Toroidal Structure of λ–Exonuclease," pp. 1824–1827.

Cold Springs Harb Symp Quant Biol, vol. 49, 1984, Clark, A.J., et al., "Genes of the RecE and RecF Pathways of Conjugational Recombination in *Escherichia coli*," pp. 453–462.

J Biol Chem, vol. 273, 1998, Noirot, P., and Kolodner, R.D., "DNA Strand Invasion Promoted by *Escherichia coli* RecT Protein," pp. 12274–12280.

J Mol Biol, vol. 254, 1995, Thresher, et al., "Electron Microscopic Visualization of RecT Protein and its Complexes with DNA," pp. 364–371.

Molecular Microbiology, vol. 11, 1994, Kolodner, et al., "Homologous pairing proteins encoded by the *Escherichia coli* recE and recT genes," p. 23–30.

Journal of Bacteriology, vol. 175, 1993, Hall, S.D., et al., "Identification adn Characterization of the *Escherichia coli* RecT Protein, a Protein Encoded by the recE Region That Promotes Renaturation of Homologous Single–Stranded DNA," pp. 277–287.

Journal of Bacteriology, vol. 173, 1991, Murphy, K.C., "λGam Protein Inhibits the Helicase and $_\chi$–Stimulated Recombination Activities of *Escherichia coli* RecBCD Enzyme," pp. 5808–5821.

Journal of Bacteriology, vol. 170, 1988, Poteete, A.R., and Fenton, A.C., "Modulation of *Escherichia coli* RecBCD Activity by the Bacteriophage λ Gam and P22 Abc Functions," pp. 2012–2021.

Annu Rev Genet, vol. 28, 1994, Myers, R.S., and Stahl, F.W., "$_\chi$ And The RecBC D Enzymen of *Escherichia coli*," pp. 49–70.

The Journal of Biological Chemistry, vol. 259. 1984, Abremski K., and Hoess, R., "Bacteriophage P1 Site–specific Recombination–Purification and Properties Of the Cre Recombinase Protein," pp. 1509–1514.

Cell, vol. 40, 1985, Andrews, B.J., et al., "The FLP Recombinase of the $2\mu$ Circle DNA of Yeast: Interaction with Its Target Sequences," p. 795–803.

Cold Spring Harb Symp Quant Biol, vol. 49, Meyer–Leon, L., et al., "Site–specific Genetic Recombination Promoted by the FLP Protein of the Yeast 2–micron Plasmid In Vitro," pp. 797–804.

Proc Natl Acad Sci USA, vol. 80, 1983, Cox, M.M., "The FLP protein of the yeast 2–$\mu$m plasmid: Expression of a eukaryotic genetic recombination system in *Escherichia coli*," pp. 4223–4227.

Curr Opin Biotechnol, vol. 9, 1998, Lie, Y.S., and Petropoulos, C.J., "Advances in quantitative PCR technology: 5' nuclease assays," pp. 43–48.

Eur J Chem, vol. 6, 2000, Tan, W., et al., "Molecular Beacons: A Novel DNA Probe for Nucleic Acid and Protein," pp. 1107–1111.

Hum Genet, vol. 96, 1995, Laan, M., et al., "Solid–phase minisequencing confirmed by FISH analysis in determination of gene copy number," pp. 275–280.

Trends in Genetics, vol. 13, 1997, Forozan, F., et al., "Genome screening by comparative genomic hybridization," pp. 405–409.

Jurnal of Cellular Biochemistry, vol. 17G, 1993, Thompson, C.T., and Gray, J.W., "Cytogenetic Profiling Using Fluorescence In Situ Hybridization (FISH) and Comparative Genomic Hybridization (CGH)," pp. 139–143.

American Journal of Pathology, vol. 145, 1994, Houldsworth, J, and Chaganti, R.S.K., "Comparative Genomic Hybridization: An Overview," p. 1253–1260.

Nature Genetics, vol. 19, 1998, Lizardi, P.M., et al., "Mutation detection and single–molecule counting using isothermal rolling–circle amplification," pp. 225–232.

Nucleic Acids Research, vol. 27, 1999, Mitra, R.D., and Church, G.M., "In situ localized amplification and contact replication of many individual DNA molecules," pp. e34.

* cited by examiner

FIGURE 3A

```
              10         20         30         40         50         60
         CCCCGGGCTT CCTGTTCTAA TAAGAATACC TCCTAGGTCC CCCATGGGCT AACCTCATCT
         GGGGCCCGAA GGACAAGATT ATTCTTATGG AGGATCCAGG GGGTACCCGA TTGGAGTAGA 70         80         90        100        110        120
         TTGGTACTCA ACAGGGGTCT TCTTTATGAG CTTCGGACCA GCTCTTTTGA TGTGGCAGGG
         AACCATGAGT TGTCCCCAGA AGAAATACTC GAAGCCTGGT CGAGAAAACT ACACCGTCCC 130        140        150        160        170        180
         ACTGACCCTG GGTGGGGAAG CCACTCAGTG CATGACCCCA GCTGGTTCAC CACATATACC
         TGACTGGGAC CCACCCCTTC GGTGAGTCAC GTACTGGGGT CGACCAAGTG GTGTATATGG 190        200        210        220        230
         ACATACTTTT CTTGCAGGTC TGGGACACAG C ATG CCC CGG GGC CCA GTG GCT GCC
         TGTATGAAAA GAACGTCCAG ACCCTGTGTC G TAC GGG GCC CCG GGT CAC CGA CGG
                                           Met Pro Arg Gly Pro Val Ala Ala>

240              250              260              270              280
     TTA CTC CTG CTG ATT CTC CAT GGA GCT TGG AGC TGC CTG GAC CTC ACT
     AAT GAG GAC GAC TAA GAG GTA CCT CGA ACC TCG ACG GAC CTG GAG TGA
     Leu Leu Leu Leu Ile Leu His Gly Ala Trp Ser Cys Leu Asp Leu Thr>

290              300              310              320              330
     TGC TAC ACT GAC TAC CTC TGG ACC ATC ACC TGT GTC CTG GAG ACA CGG
     ACG ATG TGA CTG ATG GAG ACC TGG TAG TGG ACA CAG GAC CTC TGT GCC
     Cys Tyr Thr Asp Tyr Leu Trp Thr Ile Thr Cys Val Leu Glu Thr Arg>

340              350              360              370
     AGC CCC AAC CCC AGC ATA CTC AGT CTC ACC TGG CAA GAT GAA TAT GAG
     TCG GGG TTG GGG TCG TAT GAG TCA GAG TGG ACC GTT CTA CTT ATA CTC
     Ser Pro Asn Pro Ser Ile Leu Ser Leu Thr Trp Gln Asp Glu Tyr Glu>

380              390              400              410              420
     GAA CTT CAG GAC CAA GAG ACC TTC TGC AGC CTA CAC AAG TCT GGC CAC
     CTT GAA GTC CTG GTT CTC TGG AAG ACG TCG GAT GTG TTC AGA CCG GTG
     Glu Leu Gln Asp Gln Glu Thr Phe Cys Ser Leu His Lys Ser Gly His>

430              440              450              460              470
     AAC ACC ACA CAT ATA TGG TAC ACG TGC CAT ATG CGC TTG TCT CAA TTC
     TTG TGG TGT GTA TAT ACC ATG TGC ACG GTA TAC GCG AAC AGA GTT AAG
     Asn Thr Thr His Ile Trp Tyr Thr Cys His Met Arg Leu Ser Gln Phe>

480              490              500              510              520
     CTG TCC GAT GAA GTT TTC ATT GTC AAC GTG ACG GAC CAG TCT GGC AAC
     GAC AGG CTA CTT CAA AAG TAA CAG TTG CAC TGC CTG GTC AGA CCG TTG
     Leu Ser Asp Glu Val Phe Ile Val Asn Val Thr Asp Gln Ser Gly Asn>

530              540              550              560              570
     AAC TCC CAA GAG TGT GGC AGC TTT GTC CTG GCT GAG AGC ATC AAG CCA
     TTG AGG GTT CTC ACA CCG TCG AAA CAG GAC CGA CTC TCG TAG TTC GGT
     Asn Ser Gln Glu Cys Gly Ser Phe Val Leu Ala Glu Ser Ile Lys Pro>
```

FIGURE 3B

```
            580             590             600             610
   GCT CCC CCC TTG AAC GTG ACT GTG GCC TTC TCA GGA CGC TAT GAT ATC
   CGA GGG GGG AAC TTG CAC TGA CAC CGG AAG AGT CCT GCG ATA CTA TAG
   Ala Pro Pro Leu Asn Val Thr Val Ala Phe Ser Gly Arg Tyr Asp Ile>

620             630             640             650             660
  TCC TGG GAC TCA GCT TAT GAC GAA CCC TCC AAC TAC GTG CTG AGA GGC
  AGG ACC CTG AGT CGA ATA CTG CTT GGG AGG TTG ATG CAC GAC TCT CCG
  Ser Trp Asp Ser Ala Tyr Asp Glu Pro Ser Asn Tyr Val Leu Arg Gly>

670             680             690             700             710
  AAG CTA CAA TAT GAG CTG CAG TAT CGG AAC CTC AGA GAC CCC TAT GCT
  TTC GAT GTT ATA CTC GAC GTC ATA GCC TTG GAG TCT CTG GGG ATA CGA
  Lys Leu Gln Tyr Glu Leu Gln Tyr Arg Asn Leu Arg Asp Pro Tyr Ala>

720             730             740             750             760
   GTG AGG CCG GTG ACC AAG CTG ATC TCA GTG GAC TCA AGA AAC GTC TCT
   CAC TCC GGC CAC TGG TTC GAC TAG AGT CAC CTG AGT TCT TTG CAG AGA
   Val Arg Pro Val Thr Lys Leu Ile Ser Val Asp Ser Arg Asn Val Ser>

770             780             790             800             810
   CTT CTC CCT GAA GAG TTC CAC AAA GAT TCT AGC TAC CAG CTG CAG ATG
   GAA GAG GGA CTT CTC AAG GTG TTT CTA AGA TCG ATG GTC GAC GTC TAC
   Leu Leu Pro Glu Glu Phe His Lys Asp Ser Ser Tyr Gln Leu Gln Met>

820             830             840             850
   CGG GCA GCG CCT CAG CCA GGC ACT TCA TTC AGG GGG ACC TGG AGT GAG
   GCC CGT CGC GGA GTC GGT CCG TGA AGT AAG TCC CCC TGG ACC TCA CTC
   Arg Ala Ala Pro Gln Pro Gly Thr Ser Phe Arg Gly Thr Trp Ser Glu>

860             870             880             890             900
   TGG AGT GAC CCC GTC ATC TTT CAG ACC CAG GCT GGG GAG CCC GAG GCA
   ACC TCA CTG GGG CAG TAG AAA GTC TGG GTC CGA CCC CTC GGG CTC CGT
   Trp Ser Asp Pro Val Ile Phe Gln Thr Gln Ala Gly Glu Pro Glu Ala>

910             920             930             940             950
   GGC TGG GAC CCT CAC ATG CTG CTG CTC CTG GCT GTC TTG ATC ATT GTC
   CCG ACC CTG GGA GTG TAC GAC GAC GAG GAC CGA CAG AAC TAG TAA CAG
   Gly Trp Asp Pro His Met Leu Leu Leu Leu Ala Val Leu Ile Ile Val>

960             970             980             990            1000
   CTG GTT TTC ATG GGT CTG AAG ATC CAC CTG CCT TGG AGG CTA TGG AAA
   GAC CAA AAG TAC CCA GAC TTC TAG GTG GAC GGA ACC TCC GAT ACC TTT
   Leu Val Phe Met Gly Leu Lys Ile His Leu Pro Trp Arg Leu Trp Lys>

1010            1020            1030            1040            1050
   AAG ATA TGG GCA CCA GTG CCC ACC CCT GAG AGT TTC TTC CAG CCC CTG
   TTC TAT ACC CGT GGT CAC GGG TGG GGA CTC TCA AAG AAG GTC GGG GAC
   Lys Ile Trp Ala Pro Val Pro Thr Pro Glu Ser Phe Phe Gln Pro Leu>
```

FIGURE 3C

```
          1060        1070        1080        1090
   TAC AGG GAG CAC AGC GGG AAC TTC AAG AAA TGG GTT AAT ACC CCT TTC
   ATG TCC CTC GTG TCG CCC TTG AAG TTC TTT ACC CAA TTA TGG GGA AAG
   Tyr Arg Glu His Ser Gly Asn Phe Lys Lys Trp Val Asn Thr Pro Phe>

1100        1110        1120        1130        1140
   ACG GCC TCC AGC ATA GAG TTG GTG CCA CAG AGT TCC ACA ACA ACA TCA
   TGC CGG AGG TCG TAT CTC AAC CAC GGT GTC TCA AGG TGT TGT TGT AGT
   Thr Ala Ser Ser Ile Glu Leu Val Pro Gln Ser Ser Thr Thr Thr Ser>

1150        1160        1170        1180        1190
   GCC TTA CAT CTG TCA TTG TAT CCA GCC AAG GAG AAG AAG TTC CCG GGG
   CGG AAT GTA GAC AGT AAC ATA GGT CGG TTC CTC TTC TTC AAG GGC CCC
   Ala Leu His Leu Ser Leu Tyr Pro Ala Lys Glu Lys Lys Phe Pro Gly>

1200        1210        1220        1230        1240
   CTG CCG GGT CTG GAA GAG CAA CTG GAG TGT GAT GGA ATG TCT GAG CCT
   GAC GGC CCA GAC CTT CTC GTT GAC CTC ACA CTA CCT TAC AGA CTC GGA
   Leu Pro Gly Leu Glu Glu Gln Leu Glu Cys Asp Gly Met Ser Glu Pro>

1250        1260        1270        1280        1290
   GGT CAC TGG TGC ATA ATC CCC TTG GCA GCT GGC CAA GCG GTC TCA GCC
   CCA GTG ACC ACG TAT TAG GGG AAC CGT CGA CCG GTT CGC CAG AGT CGG
   Gly His Trp Cys Ile Ile Pro Leu Ala Ala Gly Gln Ala Val Ser Ala>

1300        1310        1320        1330
   TAC AGT GAG GAG AGA GAC CGG CCA TAT GGT CTG GTG TCC ATT GAC ACA
   ATG TCA CTC CTC TCT CTG GCC GGT ATA CCA GAC CAC AGG TAA CTG TGT
   Tyr Ser Glu Glu Arg Asp Arg Pro Tyr Gly Leu Val Ser Ile Asp Thr>

1340        1350        1360        1370        1380
   GTG ACT GTG GGA GAT GCA GAG GGC CTG TGT GTC TGG CCC TGT AGC TGT
   CAC TGA CAC CCT CTA CGT CTC CCG GAC ACA CAG ACC GGG ACA TCG ACA
   Val Thr Val Gly Asp Ala Glu Gly Leu Cys Val Trp Pro Cys Ser Cys>

1390        1400        1410        1420        1430
   GAG GAT GAT GGC TAT CCA GCC ATG AAC CTG GAT GCT GGC AGA GAG TCT
   CTC CTA CTA CCG ATA GGT CGG TAC TTG GAC CTA CGA CCG TCT CTC AGA
   Glu Asp Asp Gly Tyr Pro Ala Met Asn Leu Asp Ala Gly Arg Glu Ser>

1440        1450        1460        1470        1480
   GGT CCT AAT TCA GAG GAT CTG CTC TTG GTC ACA GAC CCT GCT TTT CTG
   CCA GGA TTA AGT CTC CTA GAC GAG AAC CAG TGT CTG GGA CGA AAA GAC
   Gly Pro Asn Ser Glu Asp Leu Leu Leu Val Thr Asp Pro Ala Phe Leu>

1490        1500        1510        1520        1530
   TCT TGT GGC TGT GTC TCA GGT AGT GGT CTC AGG CTT GGG GGC TCC CCA
   AGA ACA CCG ACA CAG AGT CCA TCA CCA GAG TCC GAA CCC CCG AGG GGT
   Ser Cys Gly Cys Val Ser Gly Ser Gly Leu Arg Leu Gly Gly Ser Pro>
```

Figure 3D

```
       1540           1550           1560           1570
  GGC AGC CTA CTG GAC AGG TTG AGG CTG TCA TTT GCA AAG GAA GGG GAC
  CCG TCG GAT GAC CTG TCC AAC TCC GAC AGT AAA CGT TTC CTT CCC CTG
  Gly Ser Leu Leu Asp Arg Leu Arg Leu Ser Phe Ala Lys Glu Gly Asp>

1580           1590           1600           1610           1620
  TGG ACA GCA GAC CCA ACC TGG AGA ACT GGG TCC CCA GGA GGG GGC TCT
  ACC TGT CGT CTG GGT TGG ACC TCT TGA CCC AGG GGT CCT CCC CCG AGA
  Trp Thr Ala Asp Pro Thr Trp Arg Thr Gly Ser Pro Gly Gly Gly Ser>

1630           1640           1650           1660           1670
  GAG AGT GAA GCA GGT TCC CCC CCT GGT CTG GAC ATG GAC ACA TTT GAC
  CTC TCA CTT CGT CCA AGG GGG GGA CCA GAC CTG TAC CTG TGT AAA CTG
  Glu Ser Glu Ala Gly Ser Pro Pro Gly Leu Asp Met Asp Thr Phe Asp>

1680           1690           1700           1710           1720
  AGT GGC TTT GCA GGT TCA GAC TGT GGC AGC CCC GTG GAG ACT GAT GAA
  TCA CCG AAA CGT CCA AGT CTG ACA CCG TCG GGG CAC CTC TGA CTA CTT
  Ser Gly Phe Ala Gly Ser Asp Cys Gly Ser Pro Val Glu Thr Asp Glu>

1730           1740           1750           1760           1770
  GGA CCC CCT CGA AGC TAT CTC CGC CAG TGG GTG GTC AGG ACC CCT CCA
  CCT GGG GGA GCT TCG ATA GAG GCG GTC ACC CAC CAG TCC TGG GGA GGT
  Gly Pro Pro Arg Ser Tyr Leu Arg Gln Trp Val Val Arg Thr Pro Pro>

1780           1790           1800
  CCT GTG GAC AGT GGA GCC CAG AGC AGC TAG
  GGA CAC CTG TCA CCT CGG GTC TCG TCG ATC
  Pro Val Asp Ser Gly Ala Gln Ser Ser ***>
```

METHODS OF MODIFYING EUKARYOTIC CELLS

This application claims priority to U.S. Provisional Application No. 60/244,665 filed Oct. 31, 2000. Throughout this application various publications are referenced. The disclosure of these publications in their entireties are hereby incorporated by reference into this application.

FIELD OF THE INVENTION

The field of this invention is a method for engineering and utilizing large DNA vectors to target, via homologous recombination, and modify, in any desirable fashion, endogenous genes and chromosomal loci in eukaryotic cells. These large DNA targeting vectors for eukaryotic cells, termed LTVECs, are derived from fragments of cloned genomic DNA larger than those typically used by other approaches intended to perform homologous targeting in eukaryotic cells. The field of the invention further provides for a rapid and convenient method of detecting eukaryotic cells in which the LTVEC has correctly targeted and modified the desired endogenous gene(s) or chromosomal locus (loci). The field also encompasses the use of these cells to generate organisms bearing the genetic modification, the organisms, themselves, and methods of use thereof.

INTRODUCTION

The use of LTVECs provides substantial advantages over current methods. For example, since these are derived from DNA fragments larger than those currently used to generate targeting vectors, LTVECs can be more rapidly and conveniently generated from available libraries of large genomic DNA fragments (such as BAC and PAC libraries) than targeting vectors made using current technologies. In addition, larger modifications as well as modifications spanning larger genomic regions can be more conveniently generated than using current technologies.

Furthermore, the present invention takes advantage of long regions of homology to increase the targeting frequency of "hard to target" loci, and also diminishes the benefit, if any, of using isogenic DNA in these targeting vectors.

The present invention thus provides for a rapid, convenient, and streamlined method for systematically modifying virtually all the endogenous genes and chromosomal loci of a given organism.

BACKGROUND OF THE INVENTION

Gene targeting by means of homologous recombination between homologous exogenous DNA and endogenous chromosomal sequences has proven to be an extremely valuable way to create deletions, insertions, design mutations, correct gene mutations, introduce transgenes, or make other genetic modifications in mice. Current methods involve using standard targeting vectors, with regions of homology to endogenous DNA typically totaling less than 10–20 kb, to introduce the desired genetic modification into mouse embryonic stem (ES) cells, followed by the injection of the altered ES cells into mouse embryos to transmit these engineered genetic modifications into the mouse germline (Smithies et al., Nature, 317:230–234, 1985; Thomas et al., Cell, 51:503–512, 1987; Koller et al., Proc Natl Acad Sci USA, 86:8927–8931, 1989; Kuhn et al., Science, 254:707–710, 1991; Thomas et al., Nature, 346:847–850, 1990; Schwartzberg et al., Science, 246:799–803, 1989; Doetschman et al., Nature, 330:576–578, 1987; Thomson et al., Cell, 5:313–321, 1989; DeChiara et al., Nature, 345:78–80, 1990; U.S. Pat. No. 5,789,215, issued Aug. 4, 1998 in the name of GenPharm International). In these current methods, detecting the rare ES cells in which the standard targeting vectors have correctly targeted and modified the desired endogenous gene(s) or chromosomal locus (loci) requires sequence information outside of the homologous targeting sequences contained within the targeting vector. Assays for successful targeting involve standard Southern blotting or long PCR (Cheng, et al., Nature, 369:684–5, 1994; Foord and Rose, PCR Methods Appl, 3:S149–61, 1994; Ponce and Micol, Nucleic Acids Res, 20:623, 1992; U.S. Pat. No. 5,436,149 issued to Takara Shuzo Co., Ltd.) from sequences outside the targeting vector and spanning an entire homology arm (see Definitions); thus, because of size considerations that limit these methods, the size of the homology arms are restricted to less than 10–20 kb in total (Joyner, The Practical Approach Series, 293, 1999).

The ability to utilize targeting vectors with homology arms larger than those used in current methods would be extremely valuable. For example, such targeting vectors could be more rapidly and conveniently generated from available libraries containing large genomic inserts (e.g. BAC or PAC libraries) than targeting vectors made using current technologies, in which such genomic inserts have to be extensively characterized and trimmed prior to use. In addition, larger modifications as well as modifications spanning larger genomic regions could be more conveniently generated and in fewer steps than using current technologies. Furthermore, the use of long regions of homology could increase the targeting frequency of "hard to target" loci in eukaryotic cells, since the targeting of homologous recombination in eukaryotic cells appears to be related to the total homology contained within the targeting vector (Deng and Capecchi, Mol Cell Biol, 12:3365–71, 1992). In addition, the increased targeting frequency obtained using long homology arms could diminish any potential benefit that can be derived from using isogenic DNA in these targeting vectors.

The problem of engineering precise modifications into very large genomic fragments, such as those cloned in BAC libraries, has largely been solved through the use of homologous recombination in bacteria (Zhang, et al., Nat Genet, 20:123–8, 1998; Yang, et al., Nat Biotechnol, 15:859–65, 1997; Angrand, et al., Nucleic Acids Res, 27:e16, 1999; Muyrers, et al., Nucleic Acids Res, 27:1555–7, 1999; Narayanan, et al., Gene Ther, 6:442–7, 1999), allowing for the construction of vectors containing large regions of homology to eukaryotic endogenous genes or chromosomal loci. However, once made, these vectors have not been generally useful for modifying endogenous genes or chromosomal loci via homologous recombination because of the difficulty in detecting rare correct targeting events when homology arms are larger than 10–20 kb (Joyner, The Practical Approach Series, 293, 1999). Consequently, vectors generated using bacterial homologous recombination from BAC genomic fragments must still be extensively trimmed prior to use as targeting vectors (Hill et al., Genomics, 64:111–3, 2000). Therefore, there is still a need for a rapid and convenient methodology that makes possible the use of targeting vectors containing large regions of homology so as to modify endogenous genes or chromosomal loci in eukaryotic cells.

In accordance with the present invention, Applicants provide novel methods that enables the use of targeting vectors containing large regions of homology so as to modify endogenous genes or chromosomal loci in eukaryotic cells via homologous recombination. Such methods overcome the above-described limitations of current technologies. In addition, the skilled artisan will readily recognize that the methods of the invention are easily adapted for use with any genomic DNA of any eukaryotic organism including, but not limited to, animals such as mouse, rat, other rodent, or human, as well as plants such as soy, corn and wheat.

SUMMARY OF THE INVENTION

In accordance with the present invention, Applicants have developed a novel, rapid, streamlined, and efficient method for creating and screening eukaryotic cells which contain modified endogenous genes or chromosomal loci. This novel methods combine, for the first time:

1. Bacterial homologous recombination to precisely engineer a desired genetic modification within a large cloned genomic fragment, thereby creating a large targeting vector for use in eukaryotic cells (LTVECs);
2. Direct introduction of these LTVECs into eukaryotic cells to modify the endogenous chromosomal locus of interest in these cells; and
3. An analysis to determine the rare eukaryotic cells in which the targeted allele has been modified as desired, involving an assay for modification of allele (MOA) of the parental allele that does not require sequence information outside of the targeting sequence, such as, for example, quantitative PCR.

A preferred embodiment of the invention is a method for genetically modifying an endogenous gene or chromosomal locus in eukaryotic cells, comprising: a) obtaining a large cloned genomic fragment containing a DNA sequence of interest; b) using bacterial homologous recombination to genetically modify the large cloned genomic fragment of (a) to create a large targeting vector for use in the eukaryotic cells (LTVEC); c) introducing the LTVEC of (b) into the eukaryotic cells to modify the endogenous gene or chromosomal locus in the cells; and d) using a quantitative assay to detect modification of allele (MOA) in the eukaryotic cells of (c) to identify those eukaryotic cells in which the endogenous gene or chromosomal locus has been genetically modified.

Another embodiment of the invention is a method wherein the genetic modification to the endogenous gene or chromosomal locus comprises deletion of a coding sequence, gene segment, or regulatory element; alteration of a coding sequence, gene segment, or regulatory element; insertion of a new coding sequence, gene segment, or regulatory element; creation of a conditional allele; or replacement of a coding sequence or gene segment from one species with an homologous or orthologous coding sequence from a different species.

An alternative embodiment of the invention is a method wherein the alteration of a coding sequence, gene segment, or regulatory element comprises a substitution, addition, or fusion, wherein the fusion comprises an epitope tag or bifunctional protein.

Yet another embodiment of the invention is a method wherein the quantitative assay comprises quantitative PCR, comparative genomic hybridization, isothermic DNA amplification, or quantitative hybridization to an immobilized probe, wherein the quantitative PCR comprises TaqMan® technology or quantitative PCR using molecular beacons.

Another preferred embodiment of the invention is a method wherein the eukaryotic cell is a mammalian embryonic stem cell and in particular wherein the embryonic stem cell is a mouse, rat, or other rodent embryonic stem cell.

Another preferred embodiment of the invention is a method wherein the endogenous gene or chromosomal locus is a mammalian gene or chromosomal locus, preferably a human gene or chromosomal locus or a mouse, rat, or other rodent gene or chromosomal locus.

An additional preferred embodiment is one in which the LTVEC is capable of accommodating large DNA fragments greater than 20 kb, and in particular large DNA fragments greater than 100 kb.

Another preferred embodiment is a genetically modified endogenous gene or chromosomal locus that is produced by the method of the invention.

Yet another preferred embodiment is a genetically modified eukaryotic cell that is produced by the method of the invention.

A preferred embodiment of the invention is a non-human organism containing the genetically modified endogenous gene or chromosomal locus produced by the method of the invention.

Also preferred in a non-human organism produced from the genetically modified eukaryotic cells or embryonic stem cells produced by the method of the invention.

A preferred embodiment is a non-human organism containing a genetically modified endogenous gene or chromosomal locus, produced by a method comprising the steps of: a) obtaining a large cloned genomic fragment containing a DNA sequence of interest; b) using bacterial homologous recombination to genetically modify the large cloned genomic fragment of (a) to create a large targeting vector (LTVEC) for use in embryonic stem cells; c) introducing the LTVEC of (b) into the embryonic stem cells to modify the endogenous gene or chromosomal locus in the cells; d) using a quantitative assay to detect modification of allele (MOA) in the embryonic stem cells of (c) to identify those embryonic stem cells in which the endogenous gene or chromosomal locus has been genetically modified; e) introducing the embryonic stem cell of (d) into a blastocyst; and f) introducing the blastocyst of (e) into a surrogate mother for gestation.

An additional preferred embodiment of the invention is a non-human organism containing a genetically modified endogenous gene or chromosomal locus, produced by a method comprising the steps of: a) obtaining a large cloned genomic fragment containing a DNA sequence of interest; b) using bacterial homologous recombination to genetically modify the large cloned genomic fragment of (a) to create a large targeting vector for use in eukaryotic cells (LTVEC); c) introducing the LTVEC of (b) into the eukaryotic cells to genetically modify the endogenous gene or chromosomal locus in the cells; d) using a quantitative assay to detect modification of allele (MOA) in the eukaryotic cells of (c) to identify those eukaryotic cells in which the endogenous gene or chromosomal locus has been genetically modified; e) removing the nucleus from the eukaryotic cell of (d); f) introducing the nucleus of (e) into an oocyte; and g) introducing the oocyte of (f) into a surrogate mother for gestation.

Yet another preferred embodiment is a non-human organism containing a genetically modified endogenous gene or chromosomal locus, produced by a method comprising the steps of: a) obtaining a large cloned genomic fragment containing a DNA sequence of interest; b) using bacterial homologous recombination to genetically modify the large cloned genomic fragment of (a) to create a large targeting vector for use in eukaryotic cells (LTVEC); c) introducing the LTVEC of (b) into the eukaryotic cells to genetically modify the endogenous gene or chromosomal locus in the cells; d) using a quantitative assay to detect modification of allele (MOA) in the eukaryotic cells of (c) to identify those eukaryotic cells in which the endogenous gene or chromosomal locus has been genetically modified; e) fusing the eukaryotic cell of (d) with another eukaryotic cell; f) introducing the fused eukaryotic cell of (e) into a surrogate mother for gestation.

In preferred embodiments, the non-human organism is a mouse, rat, or other rodent; the blastocyst is a mouse, rat, or other rodent blastocyst; the oocyte is a mouse, rat, or other rodent oocyte; and the surrogate mother is a mouse, rat, or other rodent.

Another preferred embodiment is one in which the embryonic stem cell is a mammalian embryonic stem cell, preferably a mouse, rat, or other rodent embryonic stem cell.

An additional preferred embodiment is the use of the genetically modified eukaryotic cells of the invention for the production of a non-human organism, and in particular, the use of the genetically modified embryonic stem cell of the invention for the production of a non-human organism.

A preferred embodiment of the invention is a method for genetically modifying an endogenous gene or chromosomal locus of interest in mouse embryonic stem cells, comprising: a) obtaining a large cloned genomic fragment greater than 20 kb which contains a DNA sequence of interest, wherein the large cloned DNA fragment is homologous to the endogenous gene or chromosomal locus; b) using bacterial homologous recombination to genetically modify the large cloned genomic fragment of (a) to create a large targeting vector for use in the mouse embryonic stem cells, wherein the genetic modification is deletion of a coding sequence, gene segment, or regulatory element; c) introducing the large targeting vector of (b) into the mouse embryonic stem cells to modify the endogenous gene or chromosomal locus in the cells; and d) using a quantitative assay to detect modification of allele (MOA) in the mouse embryonic stem cells of (c) to identify those mouse embryonic stem cells in which the endogenous gene or chromosomal locus has been genetically modified, wherein the quantitative assay is quantitative PCR. Also preferred is a genetically modified mouse embryonic stem cell produced by this method; a mouse containing a genetically modified endogenous gene or chromosomal locus produced by this method; and a mouse produced from the genetically modified mouse embryonic stem cell.

Another preferred embodiment is a mouse containing a genetically modified endogenous gene or chromosomal locus of interest, produced by a method comprising the steps of: a) obtaining a large cloned genomic fragment greater than 20 kb which contains a DNA sequence of interest, wherein the large cloned DNA fragment is homologous to the endogenous gene or chromosomal locus; b) using bacterial homologous recombination to genetically modify the large cloned genomic fragment of (a) to create a large targeting vector for use in the mouse embryonic stem cells, wherein the genetic modification is deletion of a coding sequence, gene segment, or regulatory element; c) introducing the large targeting vector of (b) into the mouse embryonic stem cells to modify the endogenous gene or chromosomal locus in the cells; and d) using a quantitative assay to detect modification of allele (MOA) in the mouse embryonic stem cells of (c) to identify those mouse embryonic stem cells in which the endogenous gene or chromosomal locus has been genetically modified, wherein the quantitative assay is quantitative PCR; e) introducing the mouse embryonic stem cell of (d) into a blastocyst; and f) introducing the blastocyst of (e) into a surrogate mother for gestation.

Also preferred is the use of the genetically modified mouse embryonic stem cell described above for the production of a mouse.

BRIEF DESCRIPTION OF THE FIGURES

FIGS. 3A–3D (SEQ ID nos 5 and 6). Sequence of the mouse OCR10 cDNA, homology box 1 (hb1), homology box 2 (hb2), and TaqMan® probes and primers used in a quantitative PCR assay to detect modification of allele (MOA) in ES cells targeted using the mOCR10 LTVEC.

Figure 1:
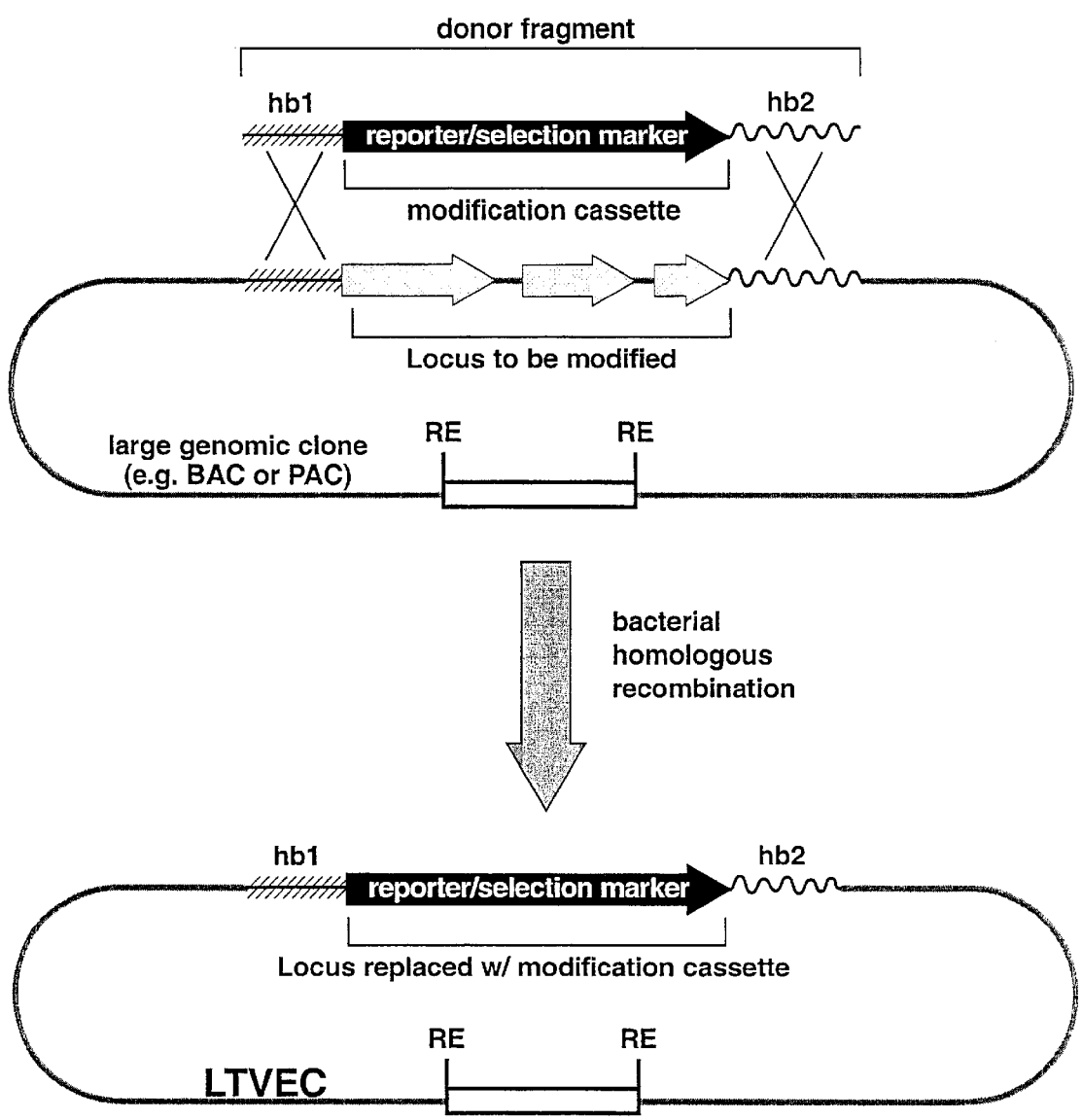
FIG. 1: Schematic diagram of the generation of a typical LTVEC using bacterial homologous recombination. (hb1=homology box 1; hb2=homology box 2; RE=restriction enzyme site).

hb1: base pairs 1 to 211
    hb2: base pairs 1586 to 1801
    TaqMan® probe and corresponding PCR primer set derived from mOCR10 exon 3:
        TaqMan® probe: nucleotides 413 to 439—upper strand
        Primer ex3-5': nucleotides 390 to 410—upper strand
        Primer ex3-3': nucleotides 445 to 461—lower strand
    TaqMan® probe and corresponding PCR primer set derived from mOCR10 exon 4:
        TaqMan® probe: nucleotides 608 to 639—upper strand
        Primer ex4-5': nucleotides 586 to 605—upper strand
        Primer ex4-3': nucleotides 642 to 662—lower strand

DEFINITIONS

A "targeting vector" is a DNA construct that contains sequences "homologous" to endogenous chromosomal nucleic acid sequences flanking a desired genetic modification(s). The flanking homology sequences, referred to as "homology arms", direct the targeting vector to a specific chromosomal location within the genome by virtue of the homology that exists between the homology arms and the corresponding endogenous sequence and introduce the desired genetic modification by a process referred to as "homologous recombination".

"Homologous" means two or more nucleic acid sequences that are either identical or similar enough that they are able to hybridize to each other or undergo intermolecular exchange.

"Gene targeting" is the modification of an endogenous chromosomal locus by the insertion into, deletion of, or replacement of the endogenous sequence via homologous recombination using a targeting vector.

A "gene knockout" is a genetic modification resulting from the disruption of the genetic information encoded in a chromosomal locus.

A "gene knockin" is a genetic modification resulting from the replacement of the genetic information encoded in a chromosomal locus with a different DNA sequence.

A "knockout organism" is an organism in which a significant proportion of the organism's cells harbor a gene knockout.

A "knockin organism" is an organism in which a significant proportion of the organism's cells harbor a gene knockin.

A "marker" or a "selectable marker" is a selection marker that allows for the isolation of rare transfected cells expressing the marker from the majority of treated cells in the population. Such marker's gene's include, but are not limited to, neomycin phosphotransferase and hygromycin B phosphotransferase, or fluorescing proteins such as GFP.

An "ES cell" is an embryonic stem cell. This cell is usually derived from the inner cell mass of a blastocyst-stage embryo.

An "ES cell clone" is a subpopulation of cells derived from a single cell of the ES cell population following introduction of DNA and subsequent selection.

A "flanking DNA" is a segment of DNA that is collinear with and adjacent to a particular point of reference.

"LTVECs" are large targeting vectors for eukaryotic cells that are derived from fragments of cloned genomic DNA larger than those typically used by other approaches intended to perform homologous targeting in eukaryotic cells.

A "non-human organism" is an organism that is not normally accepted by the public as being human.

"Modification of allele" (MOA) refers to the modification of the exact DNA sequence of one allele of a gene(s) or chromosomal locus (loci) in a genome. This modification of allele (MOA) includes, but is not limited to, deletions, substitutions, or insertions of as little as a single nucleotide or deletions of many kilobases spanning a gene(s) or chromosomal locus (loci) of interest, as well as any and all possible modifications between these two extremes.

"Orthologous" sequence refers to a sequence from one species that is the functional equivalent of that sequence in another species.

The description and examples presented infra are provided to illustrate the subject invention. One of skill in the art will recognize that these examples are provided by way of illustration only and are not included for the purpose of limiting the invention.

DETAILED DESCRIPTION OF THE INVENTION

Applicants have developed a novel, rapid, streamlined, and efficient method for creating and screening eukaryotic cells which contain modified endogenous genes or chromosomal loci. In these cells, the modification may be gene(s) knockouts, knockins, point mutations, or large genomic insertions or deletions or other modifications. By way of non-limiting example, these cells may be embryonic stem cells which are useful for creating knockout or knockin organisms and in particular, knockout or knockin mice, for the purpose of determining the function of the gene(s) that have been altered, deleted and/or inserted.

The novel methods described herein combine, for the first time:

1. Bacterial homologous recombination to precisely engineer a desired genetic modification within a large cloned genomic DNA fragment, thereby creating a large targeting vector for use in eukaryotic cells (LTVECs);
2. Direct introduction of these LTVECs into eukaryotic cells to modify the corresponding endogenous gene(s) or chromosomal locus(loci) of interest in these cells; and
3. An analysis to determine the rare eukaryotic cells in which the targeted allele has been modified as desired, involving a quantitative assay for modification of allele (MOA) of the parental allele.

It should be emphasized that previous methods to detect successful homologous recombination in eukaryotic cells cannot be utilized in conjunction with the LTVECs of Applicants' invention because of the long homology arms present in the LTVECs. Utilizing a LTVEC to deliberately modify endogenous genes or chromosomal loci in eukaryotic cells via homologous recombination is made possible by the novel application of an assay to determine the rare eukaryotic cells in which the targeted allele has been modified as desired, such assay involving a quantitative assay for modification of allele (MOA) of a parental allele, by employing, for example, quantitative PCR or other suitable quantitative assays for MOA.

The ability to utilize targeting vectors with homology arms larger than those used in current methods is extremely valuable for the following reasons:

1. Targeting vectors are more rapidly and conveniently generated from available libraries containing large genomic inserts (e.g. BAC or PAC libraries) than targeting vectors made using previous technologies, in which the genomic inserts have to be extensively characterized and "trimmed" prior to use (explained in detail below). In addition, minimal sequence information needs to be known about the locus of interest, i.e. it is only necessary to know the approximately 80–100 nucleotides that are required to generate the homology boxes (described in detail below) and to generate probes that can be used in quantitative assays for MOA (described in detail below).
2. Larger modifications as well as modifications spanning larger genomic regions are more conveniently generated and in fewer steps than using previous technologies. For example, the method of the invention makes possible the precise modification of large loci that cannot be accommodated by traditional plasmid-based targeting vectors because of their size limitations. It also makes possible the modification of any given locus at multiple points (e.g. the introduction of specific mutations at different exons of a multi-exon gene) in one step, alleviating the need to engineer multiple targeting vectors and to perform multiple rounds of targeting and screening for homologous recombination in ES cells.
3. The use of long regions of homology (long homology arms) increase the targeting frequency of "hard to target" loci in eukaryotic cells, consistent with previous findings that targeting of homologous recombination in eukaryotic cells appears to be related to the total homology contained within the targeting vector.
4. The increased targeting frequency obtained using long homology arms apparently diminishes the benefit, if any, from using isogenic DNA in these targeting vectors.
5. The application of quantitative MOA assays for screening eukaryotic cells for homologous recombination not only empowers the use of LTVECs as targeting vectors (advantages outlined above) but also reduces the time for identifying correctly modified eukaryotic cells from the typical several days to a few hours. In addition, the application of quantitative MOA does not require the use of probes located outside the endogenous gene(s) or chromosomal locus(loci) that is being modified, thus obviating the need to know the sequence flanking the modified gene(s) or locus(loci). This is a significant improvement in the way the screening has been performed in the past and makes it a much less labor-intensive and much more cost-effective approach to screening for homologous recombination events in eukaryotic cells.

Methods

Many of the techniques used to construct DNA vectors described herein are standard molecular biology techniques well known to the skilled artisan (see e.g., Sambrook, J., E. F. Fritsch And T. Maniatis. Molecular Cloning: A Laboratory Manual, Second Edition, Vols 1, 2, and 3, 1989; Current Protocols in Molecular Biology, Eds. Ausubel et al., Greene Publ. Assoc., Wiley Interscience, NY). All DNA sequencing is done by standard techniques using an ABI 373A DNA sequencer and Taq Dideoxy Terminator Cycle Sequencing Kit (Applied Biosystems, Inc., Foster City, Calif.).

Step 1. Obtain a Large Genomic DNA Clone Containing the Gene(s) or Chromosomal Locus (Loci) of Interest A Gene(s) or locus(loci) of interest can be selected based on specific criteria, such as detailed structural or functional data, or it can be selected in the absence of such detailed information as potential genes or gene fragments become predicted through the efforts of the various genome sequencing projects. Importantly, it should be noted that it is not necessary to know the complete sequence and gene structure of a gene(s) of interest to apply the method of the subject invention to produce LTVECs. In fact, the only sequence information that is required is approximately 80–100 nucleotides so as to obtain the genomic clone of interest as well as to generate the homology boxes used in making the LTVEC (described in detail below) and to make probes for use in quantitative MOA assays.

Once a gene(s) or locus(loci) of interest has been selected, a large genomic clone(s) containing this gene(s) or locus (loci) is obtained. This clone(s) can be obtained in any one of several ways including, but not limited to, screening suitable DNA libraries (e.g. BAC, PAC, YAC, or cosmid) by standard hybridization or PCR techniques, or by any other methods familiar to the skilled artisan.

Step 2. Append Homology Boxes 1 and 2 to a Modification Cassette and Generation of LTVEC Homology boxes mark the sites of bacterial homologous recombination that are used to generate LTVECs from large cloned genomic fragments (FIG. 1). Homology boxes are short segments of DNA, generally double-stranded and at least 40 nucleotides in length, that are homologous to regions within the large cloned genomic fragment flanking the "region to be modified". The homology boxes are appended to the modification cassette, so that following homologous recombination in bacteria, the modification cassette replaces the region to be modified (FIG. 1). The technique of creating a targeting vector using bacterial homologous recombination can be performed in a variety of systems (Yang et al., Nat Biotechnol, 15:859–65, 1997; Muyrers et al., Nucleic Acids Res, 27:1555–7, 1999; Angrand et al., Nucleic Acids Res, 27:e16, 1999; Narayanan et al., Gene Ther, 6:442–7, 1999; Yu, et al., Proc Natl Acad Sci U S A, 97:5978–83, 2000). One example of a favored technology currently in use is ET cloning (Zhang et al., Nat Genet, 20:123–8, 1998; Narayanan et al., Gene Ther, 6:442–7, 1999) and variations of this technology (Yu, et al., Proc Natl Acad Sci U S A, 97:5978–83, 2000). ET refers to the recE (Hall and Kolodner, Proc Natl Acad Sci USA, 91:3205–9, 1994) and recT proteins (Kusano et al., Gene, 138:17–25, 1994) that carry out the homologous recombination reaction. RecE is an exonuclease that trims one strand of linear double-stranded DNA (essentially the donor DNA fragment described infra) 5' to 3', thus leaving behind a linear double-stranded fragment with a 3' single-stranded overhang. This single-stranded overhang is coated by recT protein, which has single-stranded DNA (ssDNA) binding activity (Kovall and Matthews, Science, 277:1824–7, 1997).

ET cloning is performed using *E. coli* that transiently express the *E. coli* gene products of recE and recT (Hall and Kolodner, Proc Natl Acad Sci USA, 91:3205–9, 1994; Clark et al., Cold Spring Harb Symp Quant Biol, 49:453–62, 1984; Noirot and Kolodner, J Biol Chem, 273:12274–80, 1998; Thresher et al., J Mol Biol, 254:364–71, 1995; Kolodner et al., Mol Microbiol, 11:23–30, 1994; Hall et al., J Bacteriol, 175:277–87, 1993) and the bacteriophage lambda (λ) protein λgam (Murphy, J Bacteriol, 173:5808–21, 1991; Poteete et al., J Bacteriol, 170:2012–21, 1988). The λgam protein is required for protecting the donor DNA fragment from degradation by the recBC exonuclease system (Myers and Stahl, Annu Rev Genet, 28:49–70, 1994) and it is required for efficient ET-cloning in recBC$^+$ hosts such as the frequently used *E. coli* strain DH10b.

The region to be modified and replaced using bacterial homologous recombination can range from zero nucleotides in length (creating an insertion into the original locus) to many tens of kilobases (creating a deletion and/or a replacement of the original locus). Depending on the modification cassette, the modification can result in the following:

(a) deletion of coding sequences, gene segments, or regulatory elements;

(b) alteration(s) of coding sequence, gene segments, or regulatory elements including substitutions, additions, and fusions (e.g. epitope tags or creation of bifunctional proteins such as those with GFP);

(c) insertion of new coding regions, gene segments, or regulatory elements, such as those for selectable marker genes or reporter genes or putting new genes under endogenous transcriptional control;

(d) creation of conditional alleles, e.g. by introduction of loxP sites flanking the region to be excised by Cre recombinase (Abremski and Hoess, J Biol Chem, 259:1509–14, 1984), or FRT sites flanking the region to be excised by Flp recombinase (Andrews et al., Cell, 40:795–803, 1985; Meyer-Leon et al., Cold Spring Harb Symp Quant Biol, 49:797–804, 1984; Cox, Proc Natl Acad Sci USA, 80:4223–7, 1983); or (e) replacement of coding sequences or gene segments from one species with orthologous coding sequences from a different species, e.g. replacing a murine genetic locus with the orthologous human genetic locus to engineer a mouse where that particular locus has been 'humanized'.

Any or all of these modifications can be incorporated into a LTVEC. A specific, non-limiting example in which an endogenous coding sequence is entirely deleted and simultaneously replaced with both a reporter gene as well as a selectable marker is provided below in Example 1, as are the advantages of the method of the invention as compared to previous technologies.

Step 3. (Optional). Verify that Each LTVEC Has Been Engineered Correctly

Verify that Each LTVEC Has Been Engineered Correctly by:

a. Diagnostic PCR to verify the novel junctions created by the introduction of the donor fragment into the gene(s) or chromosomal locus(loci) of interest. The PCR fragments thus obtained can be sequenced to further verify the novel junctions created by the introduction of the donor fragment into the gene(s) or chromosomal locus (loci) of interest.

b. Diagnostic restriction enzyme digestion to make sure that only the desired modifications have been introduced into the LTVEC during the bacterial homologous recombination process.

c. Direct sequencing of the LTVEC, particularly the regions spanning the site of the modification to verify the novel junctions created by the introduction of the donor fragment into the gene(s) or chromosomal locus (loci) of interest.

Step 4. Purification, Preparation, and Linearization of LTVEC DNA for Introduction into Eukaryotic Cells.

a. Preparation of LTVEC DNA:

Prepare miniprep DNA (Sambrook, J., E. F. Fritsch And T. Maniatis. Molecular Cloning: A Laboratory Manual, Second Edition, Vols 1, 2, and 3, 1989; Tillett and Neilan, Biotechniques, 24:568–70, 572, 1998;) of the selected LTVEC and re-transform the miniprep LTVEC DNA into E. coli using electroporation (Sambrook, J., E. F. Fritsch and T. Maniatis, Molecular Cloning: A Laboratory Manual, Second Edition, Vols 1, 2, and 3, 1989). This step is necessary to get rid of the plasmid encoding the recombinogenic proteins that are utilized for the bacterial homologous recombination step (Zhang et al., Nat Genet, 20:123–8, 1998; Narayanan et al., Gene Ther, 6:442–7, 1999). It is useful to get rid of this plasmid (a) because it is a high copy number plasmid and may reduce the yields obtained in the large scale LTVEC preps; (b) to eliminate the possibility of inducing expression of the recombinogenic proteins; and (c) because it may obscure physical mapping of the LTVEC. Before introducing the LTVEC into eukaryotic cells, larger amounts of LTVEC DNA are prepared by standard methodology (Sambrook, J., E. F. Fritsch And T. Maniatis. Molecular Cloning: A Laboratory Manual, Second Edition, Vols 1, 2, and 3, 1989; Tillett and Neilan, Biotechniques, 24:568–70, 572, 1998). However, this step can be bypassed if a bacterial homologous recombination method that utilizes a recombinogenic prophage is used, i.e. where the genes encoding the recombinogenic proteins are integrated into the bacterial chromosome (Yu, et al., Proc Natl Acad Sci U S A, 97:5978–83, 2000), is used.

b. Linearizing the LTVEC DNA

To prepare the LTVEC for introduction into eukaryotic cells, the LTVEC is preferably linearized in a manner that leaves the modified endogenous gene(s) or chromosomal locus(loci) DNA flanked with long homology arms. This can be accomplished by linearizing the LTVEC, preferably in the vector backbone, with any suitable restriction enzyme that digests only rarely. Examples of suitable restriction enzymes include NotI, PacI, SfiI, SrfI, SwaI, FseI, etc. The choice of restriction enzyme may be determined experimentally (i.e. by testing several different candidate rare cutters) or, if the sequence of the LTVEC is known, by analyzing the sequence and choosing a suitable restriction enzyme based on the analysis. In situations where the LTVEC has a vector backbone containing rare sites such as CosN sites, then it can be cleaved with enzymes recognizing such sites, for example λ terminase (Shizuya et al., Proc Natl Acad Sci USA, 89:8794–7, 1992; Becker and Gold, Proc Natl Acad Sci USA, 75:4199–203, 1978; Rackwitz et al., Gene, 40:259–66, 1985).

Step 5. Introduction of LTVEC into Eukaryotic Cells and Selection of Cells where Successful Introduction of the LTVEC Has Taken Place LTVEC DNA can be introduced into eukaryotic cells using standard methodology, such as transfection mediated by calcium phosphate, lipids, or electroporation (Sambrook, J., E. F. Fritsch And T. Maniatis. Molecular Cloning: A Laboratory Manual, Second Edition, Vols 1, 2, and 3, 1989). The cells where the LTVEC has been introduced successfully can be selected by exposure to selection agents, depending on the selectable marker gene that has been engineered into the LTVEC. As a non-limiting example, if the selectable marker is the neomycin phosphotransferase (neo) gene (Beck, et al., Gene, 19:327–36, 1982), then cells that have taken up the LTVEC can be selected in G418-containing media; cells that do not have the LTVEC will die whereas cells that have taken up the LTVEC will survive (Santerre, et al., Gene, 30:147–56, 1984). Other suitable selectable markers include any drug that has activity in eukaryotic cells (Joyner, The Practical Approach Series, 293, 1999), such as hygromycin B (Santerre, et al., Gene, 30:147–56, 1984; Bernard, et al., Exp Cell Res, 158:237–43, 1985; Giordano and McAllister, Gene, 88:285–8, 1990), Blasticidin S (Izumi, et al., Exp Cell Res, 197:229–33, 1991), and other which are familiar to those skilled in the art.

Step 6. Screen for Homologous Recombination Events in Eukaryotic Cells Using Quantitative Assay for Modification of Allele (MOA)

Eukaryotic cells that have been successfully modified by targeting the LTVEC into the locus of interest can be identified using a variety of approaches that can detect modification of allele within the locus of interest and that do not depend on assays spanning the entire homology arm or arms. Such approaches can include but are not limited to:

(a) quantitative PCR using TaqMan® (Lie and Petropoulos, Curr Opin Biotechnol, 9:43–8, 1998);

(b) quantitative MOA assay using molecular beacons (Tan, et al., Chemistry, 6:1107–11, 2000)

(c) fluorescence in situ hybridization FISH (Laan, et al., Hum Genet, 96:275–80, 1995) or comparative genomic hybridization (CGH) (Forozan, et al., Trends Genet, 13:405–9, 1997; Thompson and Gray, J Cell Biochem Suppl, 139–43, 1993; Houldsworth and Chaganti, Am J Pathol, 145:1253–60, 1994);

(d) isothermic DNA amplification (Lizardi, et al., Nat Genet, 19:225–32, 1998; Mitra and Church, Nucleic Acids Res, 27:e34, 1999); and (e) quantitative hybridization to an immobilized probe(s) (Southern, J. Mol. Biol. 98: 503, 1975; Kafatos F C; Jones C W; Efstratiadis A, Nucleic Acids Res 7(6): 1541–52, 1979).

Applicants provide herein an example in which TaqMan® quantitative PCR is used to screen for successfully targeted eukaryotic cells. In this non limiting example, TaqMan® is used to identify eukaryotic cells which have undergone homologous recombination wherein a portion of one of two endogenous alleles in a diploid genome has been replaced by another sequence. In contrast to traditional methods, in which a difference in restriction fragment length spanning the entire homology arm or arms indicates the modification of one of two alleles, the quantitative TaqMan® method will detect the modification of one allele by measuring the reduction in copy number (by half) of the unmodified allele. Specifically, the probe detects the unmodified allele and not the modified allele. Therefore, the method is independent of the exact nature of the modification and not limited to the sequence replacement described in this example. TaqMan is used to quantify the number of copies of a DNA template in a genomic DNA sample, especially by comparison to a reference gene (Lie and Petropoulos, Curr Opin Biotechnol, 9:43–8, 1998). The reference gene is quantitated in the same genomic DNA as the target gene(s) or locus(loci). Therefore, two TaqMan® amplifications (each with its respective probe) are performed. One TaqMan® probe determines the "Ct" (Threshold Cycle) of the reference gene, while the other probe determines the Ct of the region of the targeted gene(s) or locus(loci) which is replaced by successful targeting. The Ct is a quantity that reflects the amount of starting DNA for each of the TaqMan® probes, i.e. a less abundant sequence requires more cycles of PCR to reach the threshold cycle. Decreasing by half the number of copies of the template sequence for a TaqMan® reaction will result in an increase of about one Ct unit. TaqMan® reactions in cells where one allele of the target gene(s) or locus(loci) has been replaced by homologous recombination will result in an increase of one Ct for the target TaqMan® reaction without an increase in the Ct for the reference gene when compared to DNA from non-targeted cells. This allows for ready detection of the modification of one allele of the gene(s) of interest in eukaryotic cells using LTVECs.

As stated above, modification of allele (MOA) screening is the use of any method that detects the modification of one allele to identify cells which have undergone homologous recombination. It is not a requirement that the targeted alleles be identical (homologous) to each other, and in fact, they may contain polymorphisms, as is the case in progeny resulting from crossing two different strains of mice. In addition, one special situation that is also covered by MOA screening is targeting of genes which are normally present as a single copy in cells, such as some of the located on the sex chromosomes and in particular, on the Y chromosome. In this case, methods that will detect the modification of the single targeted allele, such as quantitative PCR, Southern blottings, etc., can be used to detect the targeting event. It is clear that the method of the invention can be used to generate modified eukaryotic cells even when alleles are polymorphic or when they are present in a single copy in the targeted cells.

Step 8. Uses of Genetically Modified Eukaryotic Cells (a) The genetically modified eukaryotic cells generated by the methods described in steps 1 through 7 can be employed in any in vitro or in vivo assay, where changing the phenotype of the cell is desirable.

(b) The genetically modified eukaryotic cell generated by the methods described in steps 1 through 7 can also be used to generate an organism carrying the genetic modification. The genetically modified organisms can be generated by several different techniques including but not limited to:

1. Modified embryonic stem (ES) cells such as the frequently used rat and mouse ES cells. ES cells can be used to create genetically modified rats or mice by standard blastocyst injection technology or aggregation techniques (Robertson, Practical Approach Series, 254, 1987; Wood, et al., Nature, 365:87–9, 1993; Joyner, The Practical Approach Series, 293, 1999), tetraploid blastocyst injection (Wang, et al., Mech Dev, 62:137–45, 1997), or nuclear transfer and cloning (Wakayama, et al., Proc Natl Acad Sci U S A, 96:14984–9, 1999). ES cells derived from other organisms such as rabbits (Wang, et al., Mech Dev, 62:137–45, 1997; Schoonjans, et al., Mol Reprod Dev, 45:439–43, 1996) or chickens (Pain, et al., Development, 122:2339–48, 1996) or other species should also be amenable to genetic modification(s) using the methods of the invention.

2. Modified protoplasts can be used to generate genetically modified plants (for example see U.S. Pat. No. 5,350,689 "Zea mays plants and transgenic Zea mays plants regenerated from protoplasts or protoplast-derived cells", and U.S. Pat. No. 5,508, 189 "Regeneration of plants from cultured guard cell protoplasts" and references therein).

3. Nuclear transfer from modified eukaryotic cells to oocytes to generate cloned organisms with modified allele (Wakayama, et al., Proc Natl Acad Sci U S A, 96:14984–9, 1999; Baguisi, et al., Nat Biotechnol, 17:456–61, 1999; Wilmut, et al., Reprod Fertil Dev, 10:639–43, 1998; Wilmut, et al., Nature, 385:810–3, 1997; Wakayama, et al., Nat Genet, 24:108–9, 2000; Wakayama, et al., Nature, 394:369–74, 1998; Rideout, et al., Nat Genet, 24:109–10, 2000; Campbell, et al., Nature, 380:64–6, 1996).

4. Cell-fusion to transfer the modified allele to another cell, including transfer of engineered chromosome (s), and uses of such cell(s) to generate organisms carrying the modified allele or engineered chromosome(s) (Kuroiwa, et al., Nat Biotechnol, 18:1086–1090, 2000).

5. The method of the invention are also amenable to any other approaches that have been used or yet to be discovered.

While many of the techniques used in practicing the individual steps of the methods of the invention are familiar to the skilled artisan, Applicants contend that the novelty of the method of the invention lies in the unique combination of those steps and techniques coupled with the never-before-described method of introducing a LTVEC directly into eukaryotic cells to modify a chromosomal locus, and the use of quantitative MOA assays to identify eukaryotic cells which have been appropriately modified. This novel combination represents a significant improvement over previous technologies for creating organisms possessing modifications of endogenous genes or chromosomal loci.

EXAMPLES

Example 1

Engineering Mouse ES Cells Bearing a Deletion of the OCR10 Gene a. Selection of a Large Genomic DNA Clone Containing mOCR10

A Bacterial Artificial Chromosome (BAC) clone carrying a large genomic DNA fragment that contained the coding sequence of the mouse OCR10 (mOCR10) gene was obtained by screening an arrayed mouse genomic DNA BAC library (Incyte Genomics) using PCR. The primers employed to screen this library were derived from the mOCR10 gene cDNA sequence.

```
(a) OCR10.RAA   (5'-AGCTACCAGCTGCAGATGCGGGCAG-3')
                (SEQ ID NO. 1)
                and OCR10.PVIrc (5'-CTCCCCAGCCTGGGTCTGAAAGATGACG-3')
                (SEQ ID NO. 2)
                which amplifies a 102 bp DNA; and (b) OCR10.TDY   (5'-GACCTCACTTGCTACACTGACTAC-3')
                (SEQ ID NO. 3)
                and OCR10.QETrc (5'-ACTTGTGTAGGCTGCAGAAGGTCTCTTG-3')
                (SEQ ID NO. 4)
                which amplifies a 1500 bp DNA.
```

Figure 2:
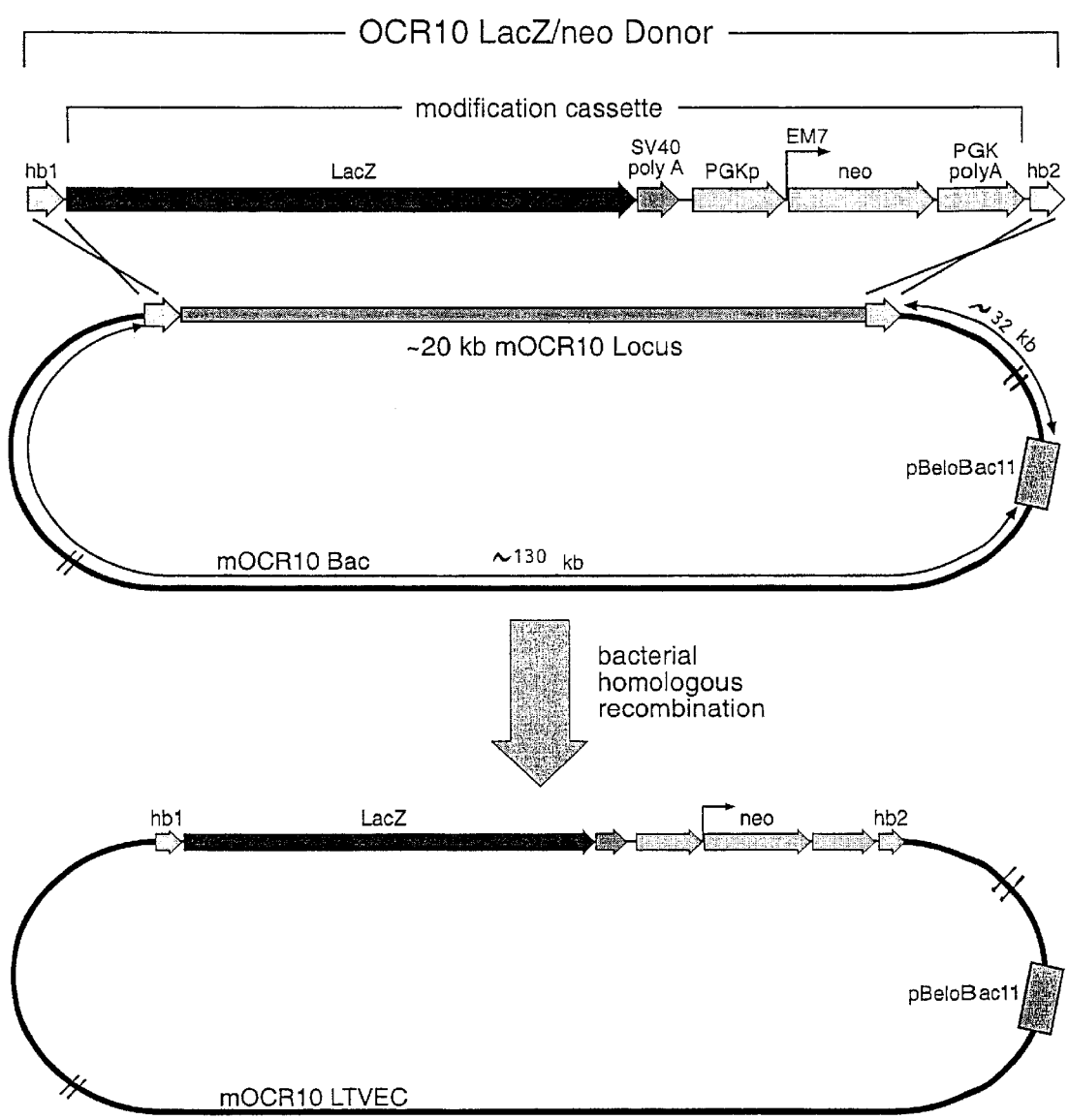
FIG. 2: Schematic diagram of donor fragment and LTVEC for mouse OCR10. (hb1=homology box 1; lacZ=β-galactosidase ORF; SV40 polyA=a DNA fragment derived from Simian Virus 40, containing a polyadenylation site and signal; PGKp=mouse phosphoglycerate kinase (PGK) promoter; EM7=a bacterial promoter; neo=neomycin phosphotransferase; PGK polyA=3' untranslated region derived from the PGK gene and containing a polyadenylation site and signal; hb2=homology box 2).

This mOCR10 BAC contained approximately 180 kb of genomic DNA including the complete mOCR10 coding sequence. This BAC clone was used to generate an LTVEC which was subsequently used to delete a portion of the coding region of mOCR10 while simultaneously introducing a reporter gene whose initiation codon precisely replaced the initiation codon of OCR10, as well as insertion of a selectable marker gene useful for selection both in *E. coli* and mammalian cells following the reporter gene (FIG. 2).

The reporter gene (in this non-limiting example LacZ, the sequence of which is readily available to the skilled artisan), encodes the E. coli β-galactosidase enzyme. Because of the position of insertion of LacZ (its initiating codon is at the same position as the initiation codon of mOCR10) the expression of lacZ should mimic that of mOCR10, as has been observed in other examples where similar replacements with LacZ were performed using previous technologies (see "Gene trap strategies in ES cells", by W Wurst and A. Gossler, in Joyner, The Practical Approach Series, 293, 1999) The LacZ gene allows for a simple and standard enzymatic assay to be performed that can reveal its expression patterns in situ, thus providing a surrogate assay that reflects the normal expression patterns of the replaced gene(s) or chromosomal locus(loci).

b. Construction of Donor Fragment and Generation of LTVEC

The modification cassette used in the construction of the mOCR10 LTVEC is the lacZ-SV40 polyA-PGKp-EM7-neo-PGK polyA cassette wherein lacZ is a marker gene as described above, SV40 polyA is a fragment derived from Simian Virus 40 (Subramanian, et al., Prog Nucleic Acid Res Mol Biol, 19:157–64, 1976; Thimmappaya, et al., J Biol Chem, 253:1613–8, 1978; Dhar, et al., Proc Natl Acad Sci U S A, 71:371–5, 1974; Reddy, et al., Science, 200:494–502, 1978) and containing a polyadenylation site and signal (Subramanian, et al., Prog Nucleic Acid Res Mol Biol, 19:157–64, 1976; Thimmappaya, et al., J Biol Chem, 253:1613–8, 1978; Dhar, et al., Proc Natl Acad Sci U S A, 71:371–5, 1974; Reddy, et al., Science, 200:494–502, 1978), PGKp is the mouse phosphoglycerate kinase (PGK) promoter (Adra, et al., Gene, 60:65–74, 1987) (which has been used extensively to drive expression of drug resistance genes in mammalian cells), EM7 is a strong bacterial promoter that has the advantage of allowing for positive selection in bacteria of the completed LTVEC construct by driving expression of the neomycin phosphotransferase (neo) gene, neo is a selectable marker that confers Kanamycin resistance in prokaryotic cells and G418 resistance in eukaryotic cells (Beck, et al., Gene, 19:327–36, 1982), and PGK polyA is a 3' untranslated region derived from the PGK gene and containing a polyadenylation site and signal (Boer, et al., Biochem Genet, 28:299–308, 1990).

To construct the mOCR10 LTVEC, first a donor fragment was generated consisting of a mOCR10 homology box 1 (hb1) attached upstream from the LacZ gene in the modification cassette and a mOCR10 homology box 2 (hb2) attached downstream of the neo-PGK polyA sequence in the modification cassette (FIG. 2), using standard recombinant genetic engineering technology. Homology box 1 (hb1) consists of 211 bp of untranslated sequence immediately upstream of the initiating methionine of the mOCR10 open reading frame (mOCR10 ORF) (FIGS. 3A–3D). Homology box 2 (hb2) consists of last 216 bp of the mOCR10 ORF, ending at the stop codon (FIGS. 3A–3D).

Subsequently, using bacterial homologous recombination (Zhang, et al., Nat Genet, 20:123–8, 1998; Angrand, et al., Nucleic Acids Res, 27:e16, 1999; Muyrers, et al., Nucleic Acids Res, 27:1555–7, 1999; Narayanan, et al., Gene Ther, 6:442–7, 1999; Yu, et al., Proc Natl Acad Sci U S A, 97:5978–83, 2000), this donor fragment was used to precisely replace the mOCR10 coding region (from initiation methionine to stop codon) with the insertion cassette, resulting in construction of the mOCR10 LTVEC (FIG. 2). Thus, in this mOCR10 LTVEC, the mOCR10 coding sequence was replaced by the insertion cassette creating an approximately 20 kb deletion in the mOCR10 locus while leaving approximately 130 kb of upstream homology (upstream homology arm) and 32 kb of downstream homology (downstream homology arm).

It is important to note that LTVECs can be more rapidly and conveniently generated from available BAC libraries than targeting vectors made using previous technologies because only a single bacterial homologous recombination step is required and the only sequence information required is that needed to generate the homology boxes. In contrast, previous approaches for generating targeting vectors using bacterial homologous recombination require that large targeting vectors be "trimmed" prior to their introduction in ES cells (Hill et al., Genomics, 64:111–3, 2000). This trimming is necessary because of the need to generate homology arms short enough to accommodate the screening methods utilized by previous approaches. One major disadvantage of the method of Hill et al. is that two additional homologous recombination steps are required simply for trimming (one to trim the region upstream of the modified locus and one to trim the region downstream of the modified locus). To do this, substantially more sequence information is needed, including sequence information spanning the sites of trimming.

In addition, another obvious advantage, illustrated by the above example, is that a very large deletion spanning the mOCR10 gene (approximately 20 kb) can be easily generated in a single step. In contrast, using previous technologies, to accomplish the same task may require several steps and may involve marking the regions upstream and downstream of the coding sequences with loxP sites in order to use the Cre recombinase to remove the sequence flanked by these sites after introduction of the modified locus in eukaryotic cells. This may be unattainable in one step, and thus may require the construction of two targeting vectors using different selection markers and two sequential targeting events in ES cells, one to introduce the loxP site at the region upstream of the coding sequence and another to introduce the loxP site at the region downstream of the coding sequence. It should be further noted that the creation of large deletions often occurs with low efficiency using the previous targeting technologies in eukaryotic cells, because the frequency of achieving homologous recombination may be low when using targeting vectors containing large deletion flanked by relatively short homology arms. The high efficiency obtained using the method of the invention (see below) is due to the very long homology arms present in the LTVEC that increase the rate of homologous recombination in eukaryotic cells.

c. Verification, Preparation, and Introduction of mOCR10 LTVEC DNA into ES Cells The sequence surrounding the junction of the insertion cassette and the homology sequence was verified by DNA sequencing. The size of the mOCR10 LTVEC was verified by restriction analysis followed by pulsed field gel electrophoresis (PFGE) (Cantor, et al., Annu Rev Biophys Biophys Chem, 17:287–304, 1988; Schwartz and Cantor, Cell, 37:67–75, 1984). A standard large-scale plasmid preparation of the mOCR10 LTVEC was done, the plasmid DNA was digested with the restriction enzyme NotI, which cuts in the vector backbone of the mOCR10 LTVEC, to generate linear DNA. Subsequently the linearized DNA was introduced into mouse ES cells by electroporation (Robertson, Practical Approach Series, 254, 1987; Joyner, The Practical Approach Series, 293, 1999; Sambrook, et al., Sambrook, J., E. F. Fritsch and T. Maniatis. Molecular Cloning: A Laboratory Manual, Second Edition, Vols 1, 2, and 3, 1989). ES cells successfully transfected with the mOCR10 LTVEC were selected for in G418-containing media using standard selection methods (Robertson, Practical Approach Series, 254, 1987; Joyner, The Practical Approach Series, 293, 1999).

d. Identification of Targeted ES Cells Clones Using a Quantitative Modification of Allele (MOA) Assay.

To identify ES cells in which one of the two endogenous mOCR10 genes had been replaced by the modification cassette sequence, DNA from individual ES cell clones was analyzed by quantitative PCR using standard TaqMan® methodology as described (Applied Biosystems, TaqMan® Universal PCR Master Mix, catalog number P/N 4304437). The primers and TaqMan® probes used are as described in FIGS. 3A–3D. A total of 69 independent ES cells clones where screened and 3 were identified as positive, i.e. as clones in which one of the endogenous mOCR10 coding sequence had been replaced by the modification cassette described above.

Several advantages of the MOA approach are apparent:
(i) It does not require the use of a probe outside the locus being modified, thus obviating the need to know the sequence flanking the modified locus.
(ii) It requires very little time to perform compared to conventional Southern blot methodology which has been the previous method of choice (Robertson, Practical Approach Series, 254, 1987, Joyner, The Practical Approach Series, 293, 1999), thus reducing the time for identifying correctly modified cells from the typical several days to just a few hours.

This is a significant improvement in the way screening has been performed in the past and makes it a much less labor-intensive and more cost-effective approach to screening for homologous recombination events in eukaryotic cells.

Yet another advantage of the method of the invention is that it is also superior to previous technologies because of its ability to target difficult loci. Using previous technologies, it has been shown that for certain loci the frequency of successful targeting may by as low as 1 in 2000 integration events, perhaps even lower. Using the method of the invention, Applicants have demonstrated that such difficult loci can be targeted much more efficiently using LTVECs that contain long homology arms (i.e. greater than those allowed by previous technologies). As the non-limiting example described above demonstrates, the Applicants have targeted the OCR10 locus, a locus that has previously proven recalcitrant to targeting using conventional technology. Using the method of the invention, Applicants have shown that they have obtained successful targeting in 3 out of 69 ES cells clones in which the mOCR10 LTVEC (containing more than 160 kb of homology arms, and introducing a 20 kb deletion) had integrated, whereas using previous technology for ES cell targeting Goyner, The Practical Approach Series, 293, 1999) using a plasmid-based vector with homology arms shorter than 10–20 kb while also introducing a deletion of less than 15 kb, no targeted events were identified among more than 600 integrants of the vector. These data clearly demonstrate the superiority of the method of the invention over previous technologies.

Example 2

Increased Targeting Frequency and Abrogation of the Need to Use Isogenic DNA when LTVECs are Used as the Targeting Vectors As noted above, the increased targeting frequency obtained using long homology arms should diminish the benefit, if any, derived from using genomic DNA in constructing LTVECs that is isogenic with (i.e. identical in sequence to) the DNA of the eukaryotic cell being targeted. To test this hypothesis, Applicants have constructed numerous LTVECs using genomic DNA derived from the same mouse substrain as the eukaryotic cell to be targeted (presumably isogenic), and numerous other LTVECs using genomic DNA derived from mouse substrains differing from that of the eukaryotic cell to be targeted (presumably non-isogenic). The two sets of LTVECs exhibited similar targeting frequencies, ranging from 1–13% (Table 1), indicating that the rate of successful targeting using LTVECs does not depend on isogenicity.

TABLE 1

SUMMARY OF GENE TARGETING USING BAC CLONE VECTORS

| | | | | Approx. (Kb) | | | | | |
|---|---|---|---|---|---|---|---|---|---|
| Target Gene | Description | DNA Origin | ES-cell | LTVEC size | Arm 1 | Arm 2 | Del | +clones | % targeting |
| NON-ISOGENIC | | | | | | | | | |
| OGH | LacZ-ATG fusion | SvJ | CJ7 | 147 | 50 | 90 | 5 | 4 | 4 |
| OCR10(A) | LacZ-ATG fusion | SvJ | CJ7 | 150 | 135 | 8 | 20 | 1 | 1.4 |
| OCR10(B) | LacZ-ATG fusion | SvJ | CJ7 | 169 | 130 | 32 | 20 | 3 | 4.3 |
| MA61 | LacZ-ATG fusion | SvJ | CJ7 | 95 | N/D | N/D | 30 | 3 | 4.6 |
| MA16 | LacZ-ATG fusion | SvJ | CJ7 | 120 | N/D | N/D | 8 | 8 | 13 |
| ISOGENIC | | | | | | | | | |
| ROR1 | Intracell-LacZ fusion | CJ7 | CJ7 | 55 | 14 | 14 | 20 | 5 | 5 |
| ROR1 | Intracell-3xmyc fusion | CJ7 | CJ7 | 55 | 14 | 14 | 20 | 2 | 2 |
| ROR2 | Brachydactyly mutation and Myc tag | CJ7 | CJ7 | 45 | 11 | 24 | 0.5 | 2 | 2 |

In summary, the approach of creating LTVECs and directly using them as targeting vectors combined with MOA screening for homologous recombination events in ES cells creates a novel method for engineering genetically modified loci that is rapid, inexpensive and represents a significant improvement over the tedious, time-consuming methods previously in use. It thus opens the possibility of a rapid large scale in vivo functional genomics analysis of essentially any and all genes in an organism's genome in a fraction of the time and cost necessitated by previous methodologies.

Although the foregoing invention has been described in some detail by way of illustration and examples, it will be readily apparent to those of ordinary skill in the art that certain changes and modifications may be made to the teachings of the invention without departing from the spirit or scope of the appended claims.

We claim:

1. A method for genetically modifying an endogenous gene or chromosomal locus of interest in isolated eukaryotic cells, comprising:
   a) obtaining a large cloned genomic fragment greater than 20 kb containing a DNA sequence of interest;
   b) using bacterial homologous recombination to genetically modify the large cloned genomic fragment of (a) to create a large targeting vector for use in eukaryotic cells (LTVEC), such LTVEC having homology arms which total greater than 20 kb;
   c) introducing the LTVEC of (b) into the isolated eukaryotic cells to modify by homologous recombination the endogenous gene or chromosomal locus in the cells; and
   d) using a quantitative assay to detect modification of allele (MOA) in the eukaryotic cells of (c) to identify those eukaryotic cells in which the endogenous gene or chromosomal locus has been genetically modified.

2. The method of claim 1 wherein the large cloned genomic fragment containing a DNA sequence is homologous to the endogenous gene or chromosomal locus of interest.

3. The method of claim 1 wherein the genetic modification to the endogenous gene or chromosomal locus comprises deletion of a coding sequence, gene segment, or regulatory element; alteration of a coding sequence, gene segment, or regulatory element; insertion of a new coding sequence, gene segment, or regulatory element; creation of a conditional allele; or replacement of a coding sequence or gene segment from one species with an homologous or orthologous coding sequence from the same or a different species.

4. The method of claim 3 wherein the alteration of a coding sequence, gene segment, or regulatory element comprises a substitution, addition, or fusion.

5. The method of claim 4 wherein the fusion comprises an epitope tag or bifunctional protein.

6. The method of claim 1 wherein the quantitative assay comprises quantitative PCR, FISH, comparative genomic hybridization, isothermic DNA amplification, or quantitative hybridization to an immobilized probe.

7. The method of claim 6 wherein the quantitative PCR comprises TaqMan® technology or quantitative PCR using molecular beacons.

8. The method of claim 1 wherein the eukaryotic cell is a mouse embryonic stem cell.

9. The method of claim 1 wherein the endogenous gene or chromosomal locus is a mammalian gene or chromosomal locus.

10. The method of claim 9 wherein the endogenous gene or chromosomal locus is a human gene or chromosomal locus.

11. The method of claim 9 wherein the endogenous gene or chromosomal locus is a mouse, rat, or other rodent gene or chromosomal locus.

12. The method of claim 1 wherein the LTVEC is capable of accommodating large DNA fragments greater than 20 kb.

13. The method of claim 12 wherein the LTVEC is capable of accommodating large DNA fragments greater than 100 kb.

14. A method for genetically modifying an endogenous gene or chromosomal locus of interest in isolated mouse embryonic stem cells, comprising:
   a) obtaining a large cloned genomic fragment greater than 20 kb which contains a DNA sequence of interest, wherein the large cloned DNA fragment is homologous to the endogenous gene or chromosomal locus;
   b) using bacterial homologous recombination to genetically modify the large cloned genomic fragment of (a) to create a large targeting vector for use in the mouse embryonic stem cells, the large targeting vector having homology arms that total greater than 20 kb and wherein the genetic modification is deletion of a coding sequence, gene segment, or regulatory element;
   c) introducing the large targeting vector of (b) into the mouse embryonic stem cells to modify by homologous recombination the endogenous gene or chromosomal locus in the cells; and
   d) using a quantitative assay to detect modification of allele (MOA) in the mouse embryonic stem cells of (c) to identify those mouse embryonic stem cells in which the endogenous gene or chromosomal locus has been genetically modified, wherein the quantitative assay is quantitative PCR.

* * * * *

SEQUENCE LISTING

<160> NUMBER OF SEQ ID NOS: 6

<210> SEQ ID NO 1
<211> LENGTH: 25
<212> TYPE: DNA
<213> ORGANISM: Artificial Sequence
<220> FEATURE:
<223> OTHER INFORMATION: Mouse OCR10 gene primer

<400> SEQUENCE: 1
agctaccagc tgcagatgcg ggcag                                       25

<210> SEQ ID NO 2
<211> LENGTH: 28
<212> TYPE: DNA
<213> ORGANISM: Artificial Sequence
<220> FEATURE:
<223> OTHER INFORMATION: Mouse OCR10 gene primer

<400> SEQUENCE: 2
ctccccagcc tgggtctgaa agatgacg                                    28

<210> SEQ ID NO 3
<211> LENGTH: 24
<212> TYPE: DNA
<213> ORGANISM: Artificial Sequence
<220> FEATURE:
<223> OTHER INFORMATION: Mouse OCR10 gene primer

<400> SEQUENCE: 3
gacctcactt gctacactga ctac                                        24

<210> SEQ ID NO 4
<211> LENGTH: 28
<212> TYPE: DNA
<213> ORGANISM: Artificial Sequence
<220> FEATURE:
<223> OTHER INFORMATION: Mouse OCR10 gene primer

<400> SEQUENCE: 4
acttgtgtag gctgcagaag gtctcttg                                    28

<210> SEQ ID NO 5
<211> LENGTH: 1799
<212> TYPE: DNA
<213> ORGANISM: Artificial Sequence
<220> FEATURE:
<223> OTHER INFORMATION: Mouse OCR10 cDNA

<400> SEQUENCE: 5
ccccgggctt cctgttctaa taagaatacc tcctaggtcc cccatgggct aacctcatct    60
ttggtactca acagggtct tctttatgag cttcggacca gctcttttga tgtggcaggg   120
actgaccctg ggtggggaag ccactcagtg catgacccca gctggttcac cacatatacc   180
acatactttt cttgcaggtc tgggacacag catgccccgg ggcccagtgg ctgccttact   240
cctgctgatt ctccatggag cttggagctg cctggacctc acttgctaca ctgactacct   300
ctggaccatc acctgtgtcc tggagacacg gagccccaac cccagcatac tcagtctcac   360
ctggcaagat gaatatgagg aacttcagga ccaagagacc ttctgcagcc tacacaagtc   420
tggccacaac accacacata tatggtacac gtgccatatg cgcttgtctc aattcctgtc   480
cgatgaagtt ttcattgtca acgtgacgga ccagtctggc aacaactccc aagagtgtgg   540

```
cagctttgtc ctggctgaga gcatcaagcc agctcccccc ttgaacgtga ctgtggcctt    600
ctcaggacgc tatgatatct cctgggactc agcttatgac gaaccctcca actacgtgct    660
gagaggcaag ctacaatatg agctgcagta tcggaacctc agagacccct atgctgtgag    720
gccggtgacc aagctgatct cagtggactc aagaaacgtc tctcctccct gaagagttcc    780
acaaagattc tagctaccag ctgcagatgc gggcagcgcc tcagccaggc acttcattca    840
gggggacctg gagtgagtgg agtgaccccg tcatctttca gacccaggct ggggagcccg    900
aggcaggctg gaccctcac atgctgctgc tcctggctgt cttgatcatt gtcctggttt    960
tcatgggtct gaagatccac ctgccttgga ggctatggaa aaagatatgg caccagtgc   1020 ccaccctga gagtttcttc cagccccgt acagggagca cagcgggaac ttcaagaaat   1080
gggttaatac ccctttcacg gcctccagca tagagttggt gccacagagt tccacaacaa   1140
catcagcctt acatctgtca ttgtatccag ccaaggagaa gaagttcccg gggctgccgg   1200
gtctggaaga gcaactggag tgtgatggaa tgtctgagcc tggtcactgg tgcataatcc   1260
ccttggcagc tggccaagcg gtctcagcct acagtgagga gagagaccgg ccatatggtc   1320
tggtgtccat tgacacagtg actgtgggag atgcagaggg cctgtgtgtc tggccctgta   1380
gctgtgagga tgatggctat ccagccatga acctggatgc tggcagagag tctggtccta   1440
attcagagga tctgctcttg gtcacagacc ctgcttttct gtcttgtggc tgtgtctcag   1500
gtagtggtct caggcttggg ggctccccag gcagcctact ggacaggttg aggctgtcat   1560
ttgcaaagga aggggactgg acagcagacc caacctggag aactgggtcc ccaggagggg   1620
gctctgagag tgaagcaggt tccccccctg gtctggacat ggacacattt gacagtggct   1680
ttgcaggttc agactgtggc agcccgtgg agactgatga aggaccccct cgaagctatc   1740
tccgccagtg ggtggtcagg acccctccac ctgtggacag tggagcccag agcagctag   1799
```

<210> SEQ ID NO 6
<211> LENGTH: 529
<212> TYPE: PRT
<213> ORGANISM: Artificial Sequence
<220> FEATURE:
<223> OTHER INFORMATION: Mouse OCR10 protein

<400> SEQUENCE: 6

```
Met Pro Arg Gly Pro Val Ala Ala Leu Leu Leu Ile Leu His Gly
1               5                  10                  15

Ala Trp Ser Cys Leu Asp Leu Thr Cys Tyr Thr Asp Tyr Leu Trp Thr
                20                  25                  30

Ile Thr Cys Val Leu Glu Thr Arg Ser Pro Asn Pro Ser Ile Leu Ser
            35                  40                  45

Leu Thr Trp Gln Asp Glu Tyr Glu Glu Leu Gln Asp Gln Glu Thr Phe
        50                  55                  60

Cys Ser Leu His Lys Ser Gly His Asn Thr Thr His Ile Trp Tyr Thr
65                  70                  75                  80

Cys His Met Arg Leu Ser Gln Phe Leu Ser Asp Glu Val Phe Ile Val
                85                  90                  95

Asn Val Thr Asp Gln Ser Gly Asn Asn Ser Gln Glu Cys Gly Ser Phe
            100                 105                 110

Val Leu Ala Glu Ser Ile Lys Pro Ala Pro Pro Leu Asn Val Thr Val
        115                 120                 125

Ala Phe Ser Gly Arg Tyr Asp Ile Ser Trp Asp Ser Ala Tyr Asp Glu
    130                 135                 140
```

-continued

```
Pro Ser Asn Tyr Val Leu Arg Gly Lys Leu Gln Tyr Glu Leu Gln Tyr
145                 150                 155                 160

Arg Asn Leu Arg Asp Pro Tyr Ala Val Arg Pro Val Thr Lys Leu Ile
                165                 170                 175

Ser Val Asp Ser Arg Asn Val Ser Leu Leu Pro Glu Glu Phe His Lys
            180                 185                 190

Asp Ser Ser Tyr Gln Leu Gln Met Arg Ala Ala Pro Gln Pro Gly Thr
        195                 200                 205

Ser Phe Arg Gly Thr Trp Ser Glu Trp Ser Asp Pro Val Ile Phe Gln
    210                 215                 220

Thr Gln Ala Gly Glu Pro Glu Ala Gly Trp Asp Pro His Met Leu Leu
225                 230                 235                 240

Leu Leu Ala Val Leu Ile Ile Val Leu Val Phe Met Gly Leu Lys Ile
                245                 250                 255

His Leu Pro Trp Arg Leu Trp Lys Lys Ile Trp Ala Pro Val Pro Thr
                260                 265                 270

Pro Glu Ser Phe Phe Gln Pro Leu Tyr Arg Glu His Ser Gly Asn Phe
            275                 280                 285

Lys Lys Trp Val Asn Thr Pro Phe Thr Ala Ser Ser Ile Glu Leu Val
        290                 295                 300

Pro Gln Ser Ser Thr Thr Thr Ser Ala Leu His Leu Ser Leu Tyr Pro
305                 310                 315                 320

Ala Lys Glu Lys Lys Phe Pro Gly Leu Pro Gly Leu Glu Glu Gln Leu
                325                 330                 335

Glu Cys Asp Gly Met Ser Glu Pro Gly His Trp Cys Ile Ile Pro Leu
                340                 345                 350

Ala Ala Gly Gln Ala Val Ser Ala Tyr Ser Glu Glu Arg Asp Arg Pro
            355                 360                 365

Tyr Gly Leu Val Ser Ile Asp Thr Val Thr Val Gly Asp Ala Glu Gly
        370                 375                 380

Leu Cys Val Trp Pro Cys Ser Cys Glu Asp Asp Gly Tyr Pro Ala Met
385                 390                 395                 400

Asn Leu Asp Ala Gly Arg Glu Ser Gly Pro Asn Ser Glu Asp Leu Leu
                405                 410                 415

Leu Val Thr Asp Pro Ala Phe Leu Ser Cys Gly Cys Val Ser Gly Ser
            420                 425                 430

Gly Leu Arg Leu Gly Gly Ser Pro Gly Ser Leu Leu Asp Arg Leu Arg
        435                 440                 445

Leu Ser Phe Ala Lys Glu Gly Asp Trp Thr Ala Asp Pro Thr Trp Arg
    450                 455                 460

Thr Gly Ser Pro Gly Gly Gly Ser Glu Ser Glu Ala Gly Ser Pro Pro
465                 470                 475                 480

Gly Leu Asp Met Asp Thr Phe Asp Ser Gly Phe Ala Gly Ser Asp Cys
                485                 490                 495

Gly Ser Pro Val Glu Thr Asp Glu Gly Pro Pro Arg Ser Tyr Leu Arg
            500                 505                 510

Gln Trp Val Val Arg Thr Pro Pro Val Asp Ser Gly Ala Gln Ser
        515                 520                 525

Ser
```